(12) United States Patent
Montes et al.

(10) Patent No.: US 8,852,558 B2
(45) Date of Patent: *Oct. 7, 2014

(54) IN SITU FORMATION OF AN ARTIFICIAL BLOCKAGE TO CONTROL BLEEDING BY POLYMER EXPANSION WITH HYDROGEN PEROXIDE AND PLATINUM CATALYST

(75) Inventors: Joseph G. Montes, Baltimore, MD (US); Krishnaswamy Kasthuri Rangan, Fairfax, VA (US); Ramachandran Radhakrishnan, Fairfax, VA (US); Tirumalai Srinivas Sudarshan, Vienna, VA (US)

(73) Assignee: Materials Modification, Inc., Fairfax, VA (US)

( * ) Notice: Subject to any disclaimer, the term of this patent is extended or adjusted under 35 U.S.C. 154(b) by 549 days.

This patent is subject to a terminal disclaimer.

(21) Appl. No.: 12/314,718

(22) Filed: Dec. 16, 2008

(65) Prior Publication Data

US 2009/0232877 A1    Sep. 17, 2009

Related U.S. Application Data

(63) Continuation-in-part of application No. 12/073,822, filed on Mar. 11, 2008.

(51) Int. Cl.

| | |
|---|---|
| *A61K 9/46* | (2006.01) |
| *A61K 9/12* | (2006.01) |
| *A61K 33/40* | (2006.01) |
| *A61P 7/04* | (2006.01) |
| *A61K 31/74* | (2006.01) |
| *A61K 31/765* | (2006.01) |
| *A61K 9/00* | (2006.01) |
| *A61L 15/18* | (2006.01) |
| *A61L 15/42* | (2006.01) |
| *A61L 26/00* | (2006.01) |

(52) U.S. Cl.
CPC ............ *A61K 31/74* (2013.01); *A61K 2201/21* (2013.01); *A61K 31/765* (2013.01); *A61K 9/0007* (2013.01); *A61K 2300/00* (2013.01); *A61K 9/0019* (2013.01); *A61K 33/40* (2013.01); *A61K 9/0024* (2013.01); *A61K 2201/045* (2013.01); *A61L 15/18* (2013.01); *A61L 15/425* (2013.01); *A61L 26/0004* (2013.01); *A61L 26/0085* (2013.01); *A61L 2400/04* (2013.01)
USPC ............... 424/44; 424/43; 424/616; 424/445; 424/423; 424/486

(58) Field of Classification Search
None
See application file for complete search history.

(56) References Cited

U.S. PATENT DOCUMENTS

| | | |
|---|---|---|
| 2,598,127 A | 5/1952 | Keckler |
| 4,030,504 A | 6/1977 | Doyle |

(Continued)

FOREIGN PATENT DOCUMENTS

WO    WO2007/088038 A1    8/2007

OTHER PUBLICATIONS

Palm, M. D. et al. Dermatol. Surg. E-pub Jan. 31, 2008; 431-445.*

(Continued)

*Primary Examiner* — Kevin S Orwig
(74) *Attorney, Agent, or Firm* — Dinesh Agarwal, P.C.

(57) ABSTRACT

A composition for in situ formation and/or expansion of a polymer-based hemostatic agent to control bleeding includes a suitable amount of a polymer or polymer-forming component, hydrogen peroxide or chemical(s) capable of forming hydrogen peroxide, or a combination of both, and a decomposing agent for hydrogen peroxide. The decomposing agent includes an endogenously or exogenously supplied catalyst (other than catalase), or both, and/or the polymer or polymer-forming component.

10 Claims, 3 Drawing Sheets

(56) References Cited

U.S. PATENT DOCUMENTS

| | | | |
|---|---|---|---|
| 4,331,653 | A | 5/1982 | Brown et al. |
| 4,377,159 | A | 3/1983 | Hansen |
| 4,948,575 | A * | 8/1990 | Cole et al. .................. 424/44 |
| 4,987,893 | A | 1/1991 | Salamone et al. |
| 5,103,812 | A | 4/1992 | Salamone et al. |
| 5,153,231 | A | 10/1992 | Bouquet et al. |
| 5,336,163 | A | 8/1994 | DeMane et al. |
| 5,507,721 | A | 4/1996 | Shippert |
| 5,667,501 | A | 9/1997 | Fowler et al. |
| 5,846,567 | A | 12/1998 | Kalloo et al. |
| 6,054,122 | A | 4/2000 | MacPhee et al. |
| 6,534,016 | B1 | 3/2003 | Cohen et al. |
| 6,627,216 | B2 | 9/2003 | Brandt et al. |
| RE38,431 | E | 2/2004 | Miekka et al. |
| 6,958,154 | B2 | 10/2005 | Andolino Brandt et al. |
| 6,964,782 | B1 * | 11/2005 | Smith et al. .................. 424/616 |
| 7,101,862 | B2 | 9/2006 | Cochrum et al. |
| 7,196,054 | B1 | 3/2007 | Drohan et al. |
| 7,226,615 | B2 | 6/2007 | Yüksel et al. |
| 7,347,850 | B2 | 3/2008 | Sawhney |
| 7,641,893 | B2 | 1/2010 | Salamone et al. |
| 7,795,326 | B2 | 9/2010 | Salamone et al. |
| 7,838,716 | B2 | 11/2010 | De Luis et al. |
| 8,025,650 | B2 | 9/2011 | Anderson et al. |
| 2003/0224054 | A1 * | 12/2003 | Gibbins et al. ............... 424/486 |
| 2005/0070616 | A1 | 3/2005 | Champ et al. |
| 2006/0142684 | A1 | 6/2006 | Shanbrom |
| 2006/0233887 | A1 | 10/2006 | Day |
| 2007/0203062 | A1 | 8/2007 | Ellis-Behnke et al. |
| 2009/0093550 | A1 | 4/2009 | Rolfes et al. |
| 2009/0202617 | A1 * | 8/2009 | Ward et al. .................. 424/447 |
| 2009/0210002 | A1 | 8/2009 | Salamone et al. |
| 2009/0232876 | A1 | 9/2009 | Montes et al. |
| 2010/0063434 | A1 | 3/2010 | Naik |
| 2010/0100022 | A1 | 4/2010 | Greener et al. |
| 2010/0234784 | A1 | 9/2010 | Hartwell |
| 2010/0292626 | A1 | 11/2010 | Gundersen et al. |
| 2011/0046262 | A1 | 2/2011 | Bublewitz et al. |
| 2011/0092871 | A1 | 4/2011 | Fabo et al. |
| 2011/0178451 | A1 | 7/2011 | Robinson et al. |
| 2011/0237994 | A1 | 9/2011 | Russ et al. |
| 2011/0275972 | A1 | 11/2011 | Rosenberg |

OTHER PUBLICATIONS

PCT International Search Report and the Written Opinion in International App. No. PCT/US09/06536 ( 8 pp.), mailed Feb. 26, 2010.

B.S. Kheirabadi, D. Tuthill, R. Pearson, V. Bayer, D. Beall, W. Drohan, M. J. MacPhee, J.B. Holcomb, Metabolic and Hemodynamic Effects of $CO_2$ Pneumoperitoneum in a Controlled Environment, *Journal of Trauma Injury, Infection and Ciritcal Care*, 50, 1031-1043 (2001).

J.B. Holcomb, J.M. McClain, A.E. Pusateri, D. Beall, J.M. Macaitis, R.A. Harris, M. J. MacPhee, J.R. Hess, Fibrin Sealant Foam Sprayed Directly on Liver Injuries Decreases Blood Loss in Resuscitated Rats *Journal of Trauma Injury, Infection and Ciritcal Care*, 49, 246-250, (2000).

D.D. Tuthill, V. Bayer, A.M. Gallagher,W.N. Drohan, M.J. MacPhee, Assessment of Topical Hemostats in a Renal Hemorrhage Model in Heparinized Rats, *Journal of Surgical Research*, 95, 126-132 (2001).

Holcomb et al. Implications of a New Dry Fibrin Sealant Technology for Trauma Surgery, *Surgical Clinics of North America*, 77, 944-952 (1997).

H.B. Alam, G. B. Uy, D. Miller, E. Koustova T. Hancock, R. Inocencio, D. Anderson, O. Llorente, P. Rhee, Comparative Analysis of Hemostatic Agents in a Swine Model of Lethal Groin Injury, *The Journal of Trauma, Injury, Infection, and Critical Care*, 54, 1077-1082 (2003).

R.G. Ellis-Behnke, Y-X. Liang, D.K.C. Tay, P.W.F. Kau, G.E. Schneider, S. Zhang, W. Wu, K.-F. So, Nano Hemostat Solution: Immediate Hemostasis at the Nanoscale, *Nanomedicine: Nanotechnology, Biology, and Medicine*; 2 , 207-215 (2006).

M.W. Chan, S.D. Schwaitzberg, M. Demcheva, J. Vournakis, S. Finkielsztein, R.J. Connolly, Comparison of Poly-N-acetyl Glucosamine with Absorbable Collagen, and Fibrin Sealant for Achieving Hemostasis in a Swine Model of Splenic Hemorrhage, *Journal of Trauma Injury, Infection and Critical Care*, 48, 454-7 (2000).

I. Wedmore, J.G. McManus, A.E. Pusateri, J.B. Holcomb, Special Report on the Chitosan-based Hemostatic Dressing: Experience in Current Combat Operations, *The Journal of Trauma Injury, Infection and Critical Care*, 60, 655-658 (2006).

A. M. Pope, Editor, Fluid Resuscitation: State of the Science for Treating Combat Casualties and Civilian Injuries, The National Academy Press, (2000).

A.E. Pusateri,J.B. Holcomb, B.S. Kheirabadi,H.B. Alam, C.E. Wade, K.L. Ryan, Making Sense of the Preclinical Literature on Advanced Hemostatic Products, *The Journal of Trauma Injury, Infection and Critical Care*, 60, 674-682, (2006).

H.B. Alam, Z. Chen, A. Jaskille,R.I.L.C. Querol, E. Koustova, R. Inocencio, R. Conran, A. Seufert, N. Ariaban, K. Toruno, P. Rhee, Application of a Zeolite Hemostatic Agent Acheives 100% Survival in a Lethal Model of Complex Groin Injury in Swine, *The Journal of Trauma Injury, Infection and Critiacal Care*, 56, 974-983, (2004).

B.S. Kheirabadi, E.M. Acheson, R. Deguzman, J.L. Sondeen, K.L. Ryan, A. Delgado A, E.J. Dick Jr, J.B. Holcomb, Hemostatic Efficacy of Two Advanced Dressings in an Aortic Hemorrhage Model in Swine, *The Journal of Trauma Injury, Infection and Critical Care*, 59, 25-34 (2005).

J.G McManus, I. Wedmore, Modern Hemostatic Agents for Hemorrhage Control—A review and Discussion of Use in Current Combat Operations, *Business Briefing: Emergency Medicine Review*,76-79 (2005).

Palm, M.D. et al. Topical Hemostatic Agents: A Review. Dermatol. Surg. E-pub Jan. 31, 2008;34; 431-445.

Costa, S.A. et al. Enzyme Immobilization in Biogradable Polymers for Biomedical Applications. Ch. 17 in Biogradable Systems in Tissue Engineering and Regenerative Medicine; Rui Reis, ed. CRC Press; 2004; 301-323.

Office Action (Restriction Requirement) dated Jul. 21, 2010, in U.S. Appl. No. 12/073,822, filed Mar. 11, 2008.

Office Action dated Jan. 12, 2011, in U.S. Appl. No. 12/073,822, filed Mar. 11, 2008.

Li X, Xu A, Xie H, Yu W, Xie W, Ma X. Preparation of low molecular weight alginate by hydrogen peroxide depolymerization for tissue engineering. Carbohydrate Polymers 79 (2010) 660-664.

PCT International Search Report and the Written Opinion in International App. No. PCT/US2012/050716 dated Oct. 19, 2012 (13 pp.) with Search History (11 pp.).

Office Action dated Aug. 9, 2011, in U.S. Appl. No. 12/073,822, filed Mar. 11, 2008.

Office Action dated Oct. 24, 2013, in U.S. Appl. No. 12/073,822, filed Mar. 11, 2008.

Office Action dated Feb. 25, 2014, in U.S. Appl. No. 13/584,852, filed Aug. 14, 2012.

Office Action (Restriction Requirement) dated Oct. 29, 2013, in U.S. Appl. No. 13/584,852, filed Aug. 14, 2012.

Haller, G. et al. Oxygen embolism after hydrogen peroxide irrigation of a vulvar abscess, *British Journal of Anaesthesia* 88 (4): 597-9 (2002).

Shetty, K. Hydrogen Peroxide Burn of the Oral Mucosa, *The Annals of Pharmacotherapy*, vol. 40, p. 351, Feb. 2006.

Rackoff, W.R. et al. Gas Embolism After Ingestion of Hydrogen Peroxide, *Pediatrics*, vol. 85, No. 4, Apr. 1990, 593-594.

Li, Y. Biological Properties of Peroxide-containing Tooth Whiteners, *Food and Chemical Toxicology* 34 (1996) 887-904.

Giberson, T.P. et al. Near-Fatal Hydrogen Peroxide Ingestion, *Annals of Emergency Medicine*, 18:7, Jul. 1989, 778-779.

* cited by examiner

IN SITU FORMATION OF AN ARTIFICIAL BLOCKAGE TO CONTROL BLEEDING BY POLYMER EXPANSION WITH HYDROGEN PEROXIDE AND PLATINUM CATALYST

CROSS-REFERENCE TO RELATED APPLICATIONS

This is a continuation-in-part (CIP) of application Ser. No. 12/073,822, filed Mar. 11, 2008, which is hereby incorporated herein in its entirety by reference.

FIELD AND BACKGROUND OF THE INVENTION

The present invention is generally directed to hemostatic compositions and methods employing the same, the delivery of agents into or unto wounds and/or body cavities, and more particularly to a composition and method for controlling bleeding at wound sites through in situ formation and expansion of a polymer-based hemostatic agent.

One of the major causes of death is uncontrolled or inadequately controlled loss of blood due to traumatic injury, accidental or otherwise. The blood loss may be internal or external and, when not restricted or controlled quickly, can be fatal. It is, therefore, critical to restrict, arrest, or control blood loss by managing a wound by, for example, creating a physical obstruction or improving the delivery of a hemostatic agent to the bleeding vessel(s). Various prior art methods and compositions disclose the medical use of hydrogen peroxide as an antiseptic for wounds or as a hemostasis-promoting agent, or as a both, e.g., U.S. Pat. No. 5,846,567, as a vapor for the dispersal or creation of a gel, and U.S. Pat. No. 5,667,501, for stimulating action of hydrogen peroxide in fibroblast proliferation and its application in wound dressing.

OBJECTS AND SUMMARY OF THE INVENTION

The principal object of the present invention is to provide a composition and method for reducing, restricting, and/or arresting, (collectively "controlling") hemorrhage from wounds, internal or external, in humans and other animals.

Another object of the present invention is to provide a composition and method for in situ formation of an artificial blockage to control bleeding.

Another object of the present invention is to provide a composition and method for a more efficient delivery of chemical and/or biological hemostatic agents to wound surfaces and other surfaces capable of absorbing the hemostatic agents.

Another object of the present invention is to provide a composition and method for controlling bleeding due to any traumatic injury, deliberate, as in a medical procedure, or accidental. The invention works by, one or more of 1) increasing the efficiency of delivery or dispersal of hemostatic and/or other wound-treatment agent(s), and/or any other clinically or medically relevant agent via the selective or non-selective expansion of substance(s) containing the agent(s); 2) providing a pressurized wound or other compartment with material that will restrict blood flow and loss within and from the compartment; 3) providing antiseptic in the form of unreacted hydrogen peroxide to the surface(s) and space(s) of a wound or other body space; 4) providing means for the creation of an artificial clot, tamponade, or obstruction that can fill the wound space or other body space efficiently; 5) providing an agent, such as hydrogen peroxide that causes or accelerates hemostasis; 6) providing excess oxygen where it may aid in initial healing; 7) in certain cases, providing the chemical basis for accelerating or making possible other chemical reactions, produced from extraneously applied chemicals or from endogenous (originating from the body itself chemicals, leading to formation of an expanding substance, foam, or obstruction to bleeding, or any combination of two or more of the three, and 8) in the case of treatment of wounds, stemming of bleeding by expanding the hemostatic material when it surrounds or encloses one or more blood vessels, including arteries and veins, thereby pinching or clamping them partially or completely.

Another object of the present invention is to provide a composition and method for controlling bleeding, which relies, in part, on an interaction between hydrogen peroxide and one or more chemical agent(s) including, but not limited to, a catalyst, or a polymer or polymer-forming agent, that is delivered to a wound or body cavity, preferably substantially simultaneously or in sequence, to produce oxygen or other gas, which serves as a blowing agent for the expansion of a polymer-based material, that in turn actively fills a wound space or other body cavity to produce a hemostatic effect or effects, or to produce other effect(s) of medical, surgical, or clinical significance. Alternatively, some, most, or all of the hydrogen peroxide may interact, instead of or in addition to, with endogenously produced catalase, the latter enzyme being released inside or upon the wound because of distribution of the leaked blood and other body fluids, so that expansion of the substance or agent applied to the wound or other body space or area will result in a fully or partially self-regulating process, whereupon the oxygen-releasing reaction(s) preferentially will occur in those locations where it is needed the most.

Another object of the present invention is to provide a composition and method for controlling bleeding, wherein one or more agents, including hydrogen peroxide, are administered to a wound or other body space or surface, causing expansion or foaming of an administered substance thereupon, due to oxygen release caused by the reaction of hydrogen peroxide with one or more catalysts, or the reaction of hydrogen peroxide with one or more polymers or polymer-forming agents. The resulting expanded substance produced by any of the aforementioned means may be a viscous liquid, semi-solid, or solid substance that acts as an artificial blood clot or clog under pressure, stemming the flow of blood from the wound, as in the case of viscous drag. Examples of such expanded substances include: polyacrylate, polyvinyl alcohol, polyvinyl pyrrolidone, polyethylene glycol, polyethylene amine, polyacrylamide, polysiloxanes, polyvinylsiloxane, vinyl polysiloxane, resins, polylysine, chitosan, polysaccharide, whey protein, casein, albumin, collagen, gelatin, a polypeptide or protein possessing reactive groups capable of cross-linking to isocyanates, diisocyanates, or other molecules, starch, cellulose, polylactic acid, polyols, an inorganic polymer, and a combination thereof. The foaming action produced by the oxygen released by the interaction between hydrogen peroxide and other chemicals may also be supplemented by the generation of another gas or other gases, or by oxygen released by another mechanism or from a substance other than hydrogen peroxide. The gas(es) generated may comprise oxygen, carbon dioxide, a nitrogen oxide, methane, ethane, ethylene, propane, or a combination thereof.

Another object of the present invention is to provide a method for increasing the temperature of the wound surface and of the associated blood for thermally accelerating the natural clotting of blood. The increase in temperature results from the exothermic chemical reactions occurring from the interaction of chemical agents present in the hemostatic composition.

Another object of the present invention is to provide a method for chemical stimulation of hemostasis by agents, including, but not limited to, hydrogen peroxide, present in a component of the invention.

Another object of the present invention is to provide a method for thermally inducing heat-shock in proteins or other indigenous biological factors, thereby improving healing of the wound subsequent to application of the invention. The increase in temperature results from the exothermic chemical reactions occurring from the interaction of chemical agents present in the hemostatic composition.

Another object of the present invention is to provide a kit for in situ formation of an artificial blockage to control bleeding in a wound or body cavity.

In summary, the present invention provides a method and composition for controlling bleeding, internal or external, by in situ formation of a blockage, and for delivering agents that are chemically and thermally hemostatic. The method may be applied consecutively more than once to the wound or body cavity, within a space of time varying between 0.1 second and one year.

One of the above objects is met, in part, by the present invention, which in one aspect includes a composition for in situ formation and expansion of a polymer-based hemostatic agent to control bleeding. The composition includes a suitable amount of a polymer or polymer-forming component, hydrogen peroxide or chemical(s) capable of forming hydrogen peroxide, or a combination of both, and a decomposing agent for hydrogen peroxide. The decomposing agent includes exogenous or endogenous catalyst other than catalase, or both. The composition may also include one or more anesthetics, one or more procoagulant(s) or coagulants, one or more vasoconstrictors, and one or more clotting agents of inorganic origin. Anesthetics may be at least one member taken from the group of tetracaine, lidocaine, benzocaine, and procaine. Procoagulants or coagulants may be at least one member from the group consisting of tissue factor, Factor VII, Factor VIIa, prothrombin, thrombin, Factor XII, Factor XIII, Factor XIIIa, fibrinogen, fibrin monomer, fibrin multimer, crosslinked fibrin, and exothermically produced heat. Vasoconstrictors may be at least one member from the group consisting of oxymetazoline, an oxymetazoline derivative, phenylephrine, phenylpropanolamine, nicotine, pseudoephedrine, ephedrine, an ephedrine derivative, and a combination thereof. Clotting agents of inorganic origin may be at least one or more agents taken from the group of silicates, peroxides, cations, anions, and inorganic polymers.

Another aspect of the present invention includes a composition for in situ formation and expansion of a polymer-based hemostatic agent to control bleeding. The composition includes a suitable amount of a polymer or polymer-forming component, hydrogen peroxide or chemical(s) capable of forming hydrogen peroxide, or a combination of both, and a decomposing agent for hydrogen peroxide. The polymer or polymer-forming agent comprises and/or also functions as the decomposing agent.

Another aspect of the present invention includes a composition for in situ formation of an artificial blockage to control bleeding, which includes an expandable component, a gas-generating agent, and an endogenous or exogenous catalyst other than catalase, or both.

Another aspect of the present invention includes a composition for in situ formation of an artificial blockage to control bleeding, which includes a polymer or polymer-forming component, a gas-generating agent, and a decomposing agent for the gas-generating agent.

Another aspect of the present invention includes a method for in situ formation of an artificial blockage in a wound or body cavity, which includes providing a suitable amount of a polymer or polymer-forming component, providing hydrogen peroxide, delivering the polymer or polymer-forming component and hydrogen peroxide in a wound or body cavity, and allowing the hydrogen peroxide to come in contact with an endogenous or exogenous catalyst other than catalase to produce an expanded mass. The polymer or polymer-forming component may be at least one member selected from the group consisting of polyacrylate, polyvinyl alcohol, polyvinyl pyrrolidone, polyethylene glycol, polyethylene amine, polyacrylamide, polysiloxanes, polyvinylsiloxane, vinyl polysiloxane, resins, polylysine, chitosan, polysaccharide, whey protein, casein, albumin, collagen, gelatin, a polypeptide or protein possessing reactive groups capable of cross-linking to isocyanates, diisocyanates, or other molecules, starch, cellulose, polylactic acid, polyols, an inorganic polymer, and a combination thereof. An optional crosslinking agent may be at least one member selected from the group consisting of phosphoric acid, boric acid, glutaraldehyde, acetaldehyde, a diisocyanate, a carbodiimide, a resin, a polymer, calcium ion, Genipin, and a combination thereof. The polymer formed comprises at least one member selected from the group consisting of polyacrylate, polyvinyl alcohol, polyvinyl pyrrolidone, polyethylene glycol, polyethylene amine, polyacrylamide, polysiloxanes, polyvinylsiloxane, vinyl polysiloxane, resins, polylysine, chitosan, polysaccharide, whey protein, casein, albumin, collagen, gelatin, a polypeptide or protein possessing reactive groups capable of cross-linking to isocyanates, diisocyanates, or other molecules, starch, cellulose, polylactic acid, polyols, an inorganic polymer, and a combination thereof.

Another aspect of the present invention includes a method for in situ formation of an artificial blockage in a wound or body cavity, which includes providing a suitable amount of a polymer or polymer-forming component, providing hydrogen peroxide, and delivering the polymer or polymer-forming component and hydrogen peroxide in a wound or body cavity and allowing a reaction therebetween to produce an expanded mass.

Another aspect of the present invention includes a method for in situ formation of an artificial blockage in a wound or body cavity, which includes providing a first component comprising a gas-generating agent, providing a second component comprising an expandable component, delivering the first and second components into a wound or body cavity, allowing the gas-generating agent to produce a gas, and allowing the gas to come in contact with the expandable component thereby producing an expanded mass.

Another aspect of the present invention includes a method for in situ formation of an artificial blockage in a wound or body cavity, which includes providing a first component comprising a gas-generating agent, providing a second component comprising an expandable component, providing a third component comprising a catalyst other than catalase, delivering the first, second and third components into a wound or body cavity, allowing the catalyst to come in contact with the gas-generating agent thereby producing a gas, and allowing the gas to come in contact with the expandable component thereby producing an expanded mass.

Another aspect of the present invention includes a kit for in situ formation of an artificial blockage in a wound or body cavity, which includes a first component including hydrogen peroxide, a second component including an expandable polymeric component, and instructions for using the components.

Another aspect of the present invention includes a kit for in situ formation of an artificial blockage in a wound or body cavity, which includes a first component including hydrogen peroxide, a second component including an expandable polymeric component, a third component including a catalyst other than catalase, and instructions for using the components.

BRIEF DESCRIPTION OF THE DRAWINGS

One of the above and other objects, aspects, novel features and advantages of the present invention will become apparent from the following detailed description of the preferred embodiment(s) of invention, illustrated in the accompanying drawings, wherein.

DETAILED DESCRIPTION OF THE PREFERRED EMBODIMENT(S) OF THE INVENTION

Figure 1:
FIG. 1 is a schematic illustration of an exemplary reaction in accordance with an embodiment of the present invention.

A preferred embodiment of the present invention is based, in part, on an interaction between hydrogen peroxide and a catalyst (other than catalase) or between hydrogen peroxide and a reactant, such as a polymer or polymer-forming agent, to generate or drive a foam, an expandable material, or other substance into a wound space or other body cavity.

One embodiment of the method described herein is conveniently referred to as hydrogen peroxide reaction-driven expansion, dispersal, and spatial configuring of wound with hemostatic and/or other wound treatment agent(s) that can be delivered into any body cavity or space, including wounds. The method can be applied to both humans and animals.

The method allows filling of wound or other space, including a body space or cavity, open to the air or otherwise, to allow coating of a body surface with a substance in the form of foam, sponge, or other material by pressure produced through the release of oxygen or other gas consequent to the reaction of a chemical component delivered at the same or about the same time as hydrogen peroxide. With this method, an agent or substance, containing hydrogen peroxide, when injected through the opening of a wound or other space or cavity in the body, will expand, disperse, or configure (collectively "expand") to fill the wound or other space, when the agent encounters one or more of the following: another substantially simultaneously delivered agent, such as a polymer or polymer-forming agent, or a catalyst, for polymer formation and/or the breakdown of hydrogen peroxide, and a wound surface or space, blood, or another body fluid, thus assisting hemostasis by effecting an improved delivery of a hemostatic agent, while at the same time causing a pressurized obstruction to bleeding or other physiological flow.

Alternatively, a binary or ternary system of two or three components, respectively, preferably one containing a catalyst (other than catalase) and/or other chemical capable of reacting catalytically or otherwise with hydrogen peroxide, when injected or forced into a wound space or other body cavity substantially simultaneously, will react to drive, separately or together, the two or three components of the system, or their reaction products, into or unto the wound or other body space, distributing the agents to where most needed, while at the same time creating a physical obstruction that restricts blood loss. Specifically, a two-component system will preferably include hydrogen peroxide and a polymer or polymer-forming agent, while a three-component system will add a catalyst (other than catalase) as the third component.

One embodiment of a method for delivery of the hydrogen peroxide and other substances into the wound or other body space will preferably be effected through compression of a pliable tube or piston-dependent delivery system containing the deliverable agents, so that hydrogen peroxide and other agents will pass into the wound space or other body space, although other suitable means may also be employed. Typically, one or more small tubing extension(s) or mixer(s) from the delivery device will be fed into the wound or other body area or space to accomplish the method. Once the agent, containing the hydrogen peroxide, makes contact with an agent capable of reacting with hydrogen peroxide to release oxygen or other gas, foaming or expansion of the applied agent will result, filling the space in the wound or other body space. The foam may, over time, harden or become more viscous, including transforming from one phase to another, such as from liquid to semi-solid or solid, and may include polymer(s) or polymer-forming ingredient(s), creating an artificial clot or clog, driven into place and shaped by the release of oxygen and/or other gas resulting from the interaction between hydrogen peroxide and a catalyst other than catalase, and/or partially or completely from the interaction between hydrogen peroxide and other agent(s) comprising the hemostatic product. The method may be applied consecutively more than once to the wound or body cavity, within a space of time varying between 0.1 second and one year.

Preferably, two or three components will be mixed just prior to or after injection, insertion, or any other kind of application to a wound space. At least one of these binary or ternary components will contain hydrogen peroxide at a concentration of about 0.000001% to about 100% by volume or weight, with a preferred range of about 1% to about 20%, and a more preferred concentration being about 2%.

One embodiment of the composition of the present invention preferably includes at least one expandable component, such as a polymer, polymer precursor or polymer-forming agent taken from the group consisting of: polyacrylate, polyvinyl alcohol, polyvinyl pyrrolidone, polyethylene glycol, polyethylene amine, polyacrylamide, polysiloxanes, polyvinylsiloxane, vinyl polysiloxane, resins, polylysine, chitosan, polysaccharide, whey protein, casein, albumin, collagen, gelatin, a polypeptide or protein possessing reactive groups capable of cross-linking to isocyanates, diisocyanates, or other molecules, starch, cellulose, polylactic acid, polyols, an inorganic polymer, and a combination thereof; a gas-generating component, such as hydrogen peroxide; and a decomposing agent for the gas-generating agent. The decomposing agent includes an endogenous or exogenous catalyst, or both, and/or at least one polymer or polymer-forming agent, as noted before. Thus, the polymer or polymer-forming agent also functions as a decomposing agent.

The catalyst(s) used in an embodiment of the composition of the present invention, includes a metal ion, platinum, triethylenediamine (TEDA, also known as 1,4-diazabicyclo[2.2.2]octane or DABCO), dimethylcyclohexylamine (DMCHA), dimethylethanolamine (DMEA), tetramethylbutanediamine (TMBDA), pentamethyldipropylenetriamine, N-(3-dimethylaminopropyl)-N,N-diisopropanolamine, 1,3,5-(tris(3-dimethylamino)propyl)-hexahydro-s-triazine, bis-(2-dimethylaminoethyl)ether, N-ethylmorpholine, triethylamine(TEA), 1,8-diazabicyclo [5.4.0]undecene-7 (DBU), pentamethyldiethylenetriamine (PMDETA), benzyldimethylamine (BDMA), tetracaine, and a combination thereof. The catalyst concentration can range from 0 to about 5,000 milligrams/mL, with a preferred range of about 50 milligrams/mL to about 350 milligrams/mL and a more preferred concentration of about 150 milligrams/mL.

The medium bearing the components delivered by an embodiment of the method of the invention can be of any state of matter, including liquid, gas, or solid, or any combination thereof.

Other agents in the composition may include polymers, organic or inorganic, polymer-forming ingredients, pre-polymers, linking agents, gas-generating agents other than hydrogen peroxide or catalase, procoagulants, coagulants, anesthetics, vasoconstrictors, catalysts other than catalase, enzymes other than catalase, pastes, liquids, organic or inorganic.

Figure 2:
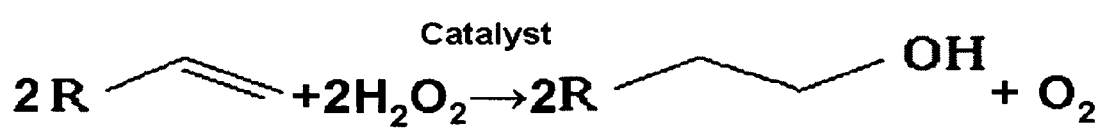
FIG. 2 is a schematic illustration of another exemplary reaction between various components in accordance with another embodiment of the present invention.

Examples of hydrogen peroxide decomposing in the presence of a catalyst, and a chemical reaction between hydrogen peroxide and a matrix component of an embodiment of the composition used in the preferred method, are shown in FIGS. 1 and 2, respectively.

Non-limiting examples of polymer-forming polymers, include: polyacrylate, polyvinyl alcohol, polyvinyl pyrrolidone, polyethylene glycol, polyethylene amine, polyacrylamide, polysiloxanes, polyvinylsiloxane, vinyl polysiloxane, resins, polylysine, chitosan, polysaccharide, whey protein, casein, albumin, collagen, gelatin, a polypeptide or protein possessing reactive groups capable of cross-linking to isocyanates, diisocyanates, or other molecules, starch, cellulose, polylactic acid, polyols, an inorganic polymer, and a combination thereof.

Non-limiting examples of optional crosslinking agents, include: phosphoric acid, boric acid, glutaraldehyde, acetaldehyde, a diisocyanate, a carbodiimide, a resin, a polymer, calcium ion, Genipin, and a combination thereof.

Non-limiting examples of coagulants and procoagulants, include: tissue factor, Factor VII, Factor VIIa, hydrogen peroxide, prothrombin, thrombin, Factor XII, Factor XIII, Factor XIIIa, fibrinogen, fibrin monomer, fibrin multimer, crosslinked fibrin, and exothermically produced heat.

Non-limiting examples of vasoconstrictors, include: oxymetazoline, oxymetazoline derivatives, phenylephrine, phenylpropanolamine, nicotine, pseudoephedrine, ephedrine, and ephedrine derivatives.

The system used to deliver any of the above-mentioned agents, including the agent hydrogen peroxide, to a wound or body cavity can be of any kind or property. The volume of the component(s) to be delivered, or the total volume of component(s) actually delivered, can range from about 0.0000001 to about 10,000,000 milliliters (mL), with a preferred range of about 5 mL to about 60 mL, and a more preferred volume of about 30 mL.

After allowing some time, preferably about 5 seconds to three minutes, or more preferably about 45 seconds, for expansion or pressurization of the component(s) or resulting component(s) in the wound space or body cavity, the wound will be sealed with a suitable bandage. The amount of time before application of the bandage can be from 0 to about 1,000,000 seconds (sec) after delivery of the component(s), with a preferred range of about 1 sec to about 15 minutes (min), and a more preferred interval of about 5 min.

Figure 3:
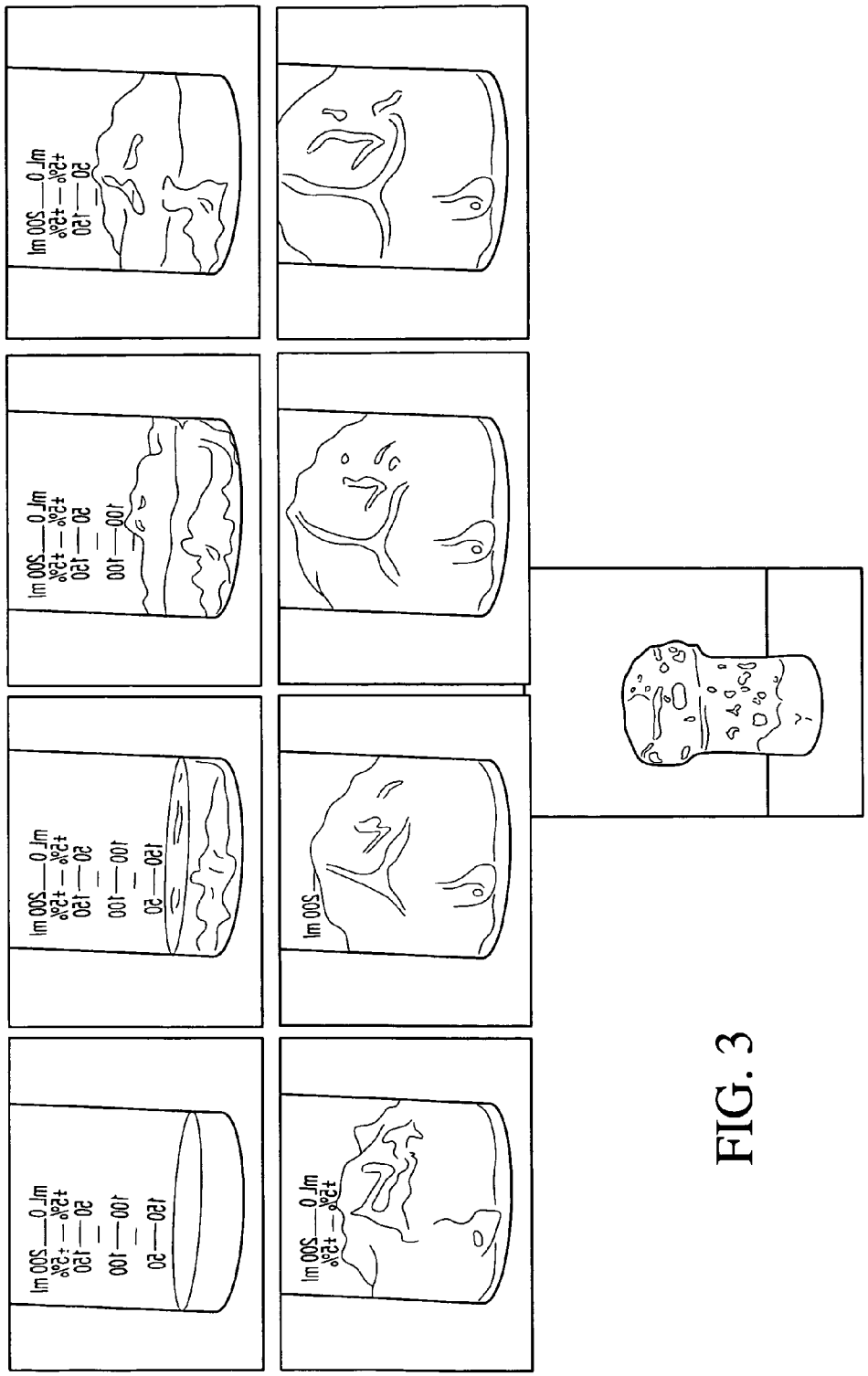
FIG. 3 is an illustration of a formative action of the composition in accordance with an embodiment of the invention, showing expansion due to the interaction between hydrogen peroxide and a polymer and/or catalyst, such as platinum.

An example of the mechanism of formation of the clotting material that fills the wound and enhances delivery of matrix components, is illustrated in FIG. 3.

The composition of the present invention can be of any chemical or physical nature or properties, and may include any organic or inorganic substance or combination of substances.

While this invention has been described as having preferred sequences, ranges, steps, materials, structures, components, features, and/or designs, it is understood that it is capable of further modifications, uses, and/or adaptations of the invention following in general the principle of the invention, and including such departures from the present disclosure as those come within the known or customary practice in the art to which the invention pertains, and as may be applied to the central features hereinbeforesefforth, and fall within the scope of the invention and of the limits of the appended claims.

REFERENCES

The following references, and any cited in the disclosure herein, are hereby incorporated herein in their entirety by reference.

1. A. Brandt, C. M. Leir, D. J. Wirtanen, Spray Bandage and Drug Delivery System, U.S. Pat. No. 6,958,154 (2005).
2. M. J. MacPhee, W. N. Drohan, C. J. Woolverton, Supplemented and Unsupplemented Tissue Sealants, Methods of their Production and Use, U.S. Pat. No. 6,054,122 (2000).
3. W. N. Drohan, M. J. MacPhee, H. Nunez, G. Liau, T. Maciag, W. H. Burgess, Methods for Treating Wound Tissue and Forming a Supplemented Fibrin Matrix U.S. Pat. No. 7,196,054 (2007).
4. S. I. Miekka, W. N. Drohan, T. R. Jameson, J. R. Taylor, Jr., M. P. Singh, M. J. MacPhee, Methods of Production and use of Liquid Formulations of Plasma Proteins U.S. Pat. RE38431 (2004).
5. K. C. Cochrum, S. Jemtrud, Hemostatic Compositions and Methods for Controlling Bleeding U.S. Pat. No. 7,101,862 (2006).
6. A. N. Kaloo, P. J. Paricha, Clot Dissolving Method, U.S. Pat. No. 5,846,567 (1998).
7. M. Fowler, T. R. Burrow, T. D. Turner, R. J. Schmidt, L. Y. Chung, Wound Dressings, U.S. Pat. No. 5,667,501 (1997).
8. B. S. Kheirabadi, D. Tuthill, R. Pearson, V. Bayer, D. Beall, W. Drohan, M. J. MacPhee, J. B. Holcomb, Metabolic and Hemodynamic Effects of $CO_2$ Pneumoperitoneum in a Controlled Environment, *Journal of Trauma Injury, Infection and Critical Care*, 50, 1031-1043 (2001).
9. J. B. Holcomb, J. M. McClain, A. E. Pusateri, D. Beall, J. M. Macaitis, R. A. Harris, M. J. MacPhee, J. R. Hess, Fibrin Sealant Foam Sprayed Directly on Liver Injuries Decreases Blood Loss in Resuscitated Rats *Journal of Trauma Injury, Infection and Critical Care*, 49, 246-250, (2000).
10. D. D. Tuthill, V. Bayer, A. M. Gallagher, W. N. Drohan, M. J. MacPhee, Assessment of Topical Hemostats in a Renal Hemorrhage Model in Heparinized Rats, *Journal of Surgical Research*, 95, 126-132 (2001).
11. Holcomb et al. Implications of a New Dry Fibrin Sealant Technology for Trauma Surgery, *Surgical Clinics of North America*, 77, 944-952 (1997).
12. H. B. Alam, G. B. Uy, D. Miller, E. Koustova, T. Hancock, R. Inocencio, D. Anderson, O. Llorente, P. Rhee, Comparative Analysis of Hemostatic Agents in a Swine Model of Lethal Groin Injury, *The Journal of TRAUMA, Injury, Infection, and Critical Care*, 54, 1077-1082 (2003).
13. R. G. Ellis-Behnke, Y-X. Liang, D. K. C. Tay, P. W. F. Kau, G. E. Schneider, S. Zhang, W. Wu, K-F. So, Nano Hemostat Solution: Immediate Hemostas is at the Nanoscale, *Nanomedicine: Nanotechnology, Biology, and Medicine;* 2, 207-215 (2006).

14. M. W. Chan, S. D. Schwaitzberg, M. Demcheva, J. Vournakis, S. Finkielsztein, R. J. Connolly, Comparison of Poly-N-acetyl Glucosamine with Absorbable Collagen, and Fibrin Sealant for Achieving Hemostasis in a Swine Model of Splenic Hemorrhage, *Journal of Trauma Injury, Infection and Critical Care,* 48, 454-7 (2000).

15. I. Wedmore, J. G. McManus, A. E. Pusateri, J. B. Holcomb, Special Report on the Chitosan-based Hemostatic Dressing: Experience in Current Combat Operations, *The Journal of Trauma Injury, Infection and Critical Care,* 60, 655-658 (2006).

16. A. M. Pope, Editor, Fluid Resuscitation: State of the Science for Treating Combat Casualties and Civilian Injuries, The National Academy Press, (2000).

17. A. E. Pusateri, J. B. Holcomb, B. S. Kheirabadi, H. B. Alam, C. E. Wade, K. L. Ryan, Making Sense of the Preclinical Literature on Advanced Hemostatic Products, *The Journal of Trauma Injury, Infection and Critical Care,* 60, 674-682, (2006).

18. H. B. Alam, Z. Chen, A. Jaskille, R. I. L. C. Querol, E. Koustova, R. Inocencio, R. Conran, A. Seufert, N. Ariaban, K. Toruno, P. Rhee, Application of a Zeolite Hemostatic Agent Achieves 100% Survival in a Lethal Model of Complex Groin Injury in Swine, *The Journal of Trauma Injury, Infection and Critical Care,* 56, 974-983, (2004).

19. B. S. Kheirabadi, E. M. Acheson, R. Deguzman, J. L. Sondeen, K. L. Ryan, A. Delgado, E. J. Dick Jr., J. B. Holcomb, Hemostatic Efficacy of Two Advanced Dressings in an Aortic Hemorrhage Model in Swine, *The Journal of Trauma Injury, Infection and Critical Care,* 59, 25-34 (2005).

20. J. G. McManus, I. Wedmore, Modern Hemostatic Agents for Hemorrhage Control—A Review and Discussion of Use in Current Combat Operations, *Business Briefing: Emergency Medicine Review,* 76-79 (2005).

21. J. G. Montes, K. K. Rangan, R. Radhakrishnan, T. S. Sudarshan, Method and Composition for In Situ Formation of an Artificial Blockage to Control Bleeding, U.S. patent application Ser. No. 12/073,822 (2008).

What is claimed is:

1. An injection method for in situ formation of a pressurized obstruction in a wound or bleeding body cavity to control bleeding, comprising the steps of:
   a) providing a polymer-forming component comprising polyvinylsiloxane;
   b) providing hydrogen peroxide having a concentration of about 20% to about 100% by volume or weight;
   c) delivering the polymer-forming component and hydrogen peroxide by injection into the wound or body cavity; and
   d) allowing the hydrogen peroxide to come in contact with an endogenous or exogenous catalyst comprising platinum, thereby producing an expanded mass within 5 seconds to 45 seconds forming a pressurized obstruction to control bleeding in the wound or body cavity.

2. The method of claim 1, wherein:
   the polymer-forming component and hydrogen peroxide are provided in a volume of about 0.1 mL to about 1000 mL.

3. The method of claim 1, wherein:
   the method may be applied consecutively more than once to the wound or body cavity, within a space of time varying between 0.1 second and one year.

4. An injection method for in situ formation of a pressurized obstruction in a wound or bleeding body cavity to control bleeding, comprising the steps of:
   a) providing a first component comprising hydrogen peroxide having a concentration of about 20% to about 100% by volume or weight;
   b) providing a second component comprising an expandable component comprising polyvinylsiloxane;
   c) providing a third component comprising a catalyst comprising platinum;
   d) delivering the first, second and third components by injection into the wound or body cavity;
   e) allowing the catalyst comprising platinum to come in contact with the hydrogen peroxide thereby producing a gas; and
   f) allowing the gas to come in contact with the polyvinylsiloxane thereby producing an expanded mass within 5 seconds to 45 seconds forming a pressurized obstruction to control bleeding in the wound or body cavity.

5. The method of claim 4, wherein:
   the first, second and third components are provided in a volume of about 0.1 mL to about 1000 mL.

6. The method of claim 4, wherein:
   the method may be applied consecutively more than once to the wound or body cavity, within a space of time varying between 0.1 second and one year.

7. The method of claim 1, wherein:
   the polymer-forming component additionally comprises at least one member selected from the group consisting of polyurethane, polysiloxane, polyacrylate, siloxane, vinyl polysiloxane, resin, an inorganic polymer, and a combination thereof.

8. The method of claim 1, wherein:
   the catalyst additionally comprises at least one member selected from the group consisting of a metal ion, triethylenediamine (TEDA, also known as 1,4-diazabicyclo[2.2.2]octane or DABCO), dimethylcyclohexylamine (DMCHA), dimethylethanolamine (DMEA), tetramethylbutanediamine (TMBDA), pentamethyldipropylenetriamine, N-(3-dimethylaminopropyl)-N,N-diisopropanolamine, 1,3,5-(tris(3-dimethylamino)propyl)-hexahydro-s-triazine, bis-(2-dimethylaminoethyl)ether, N-ethylmorpholine, triethylamine(TEA), 1,8-diazabicyclo[5.4.0]undecene-7 (DBU), pentamethyldiethylenetriamine (PMDETA), benzyldimethylamine (BDMA), tetracaine, and a combination thereof.

9. The method of claim 1, wherein:
   the expanded mass substantially entirely fills up the wound or body cavity.

10. The method of claim 1, wherein:
    the expanded mass configures to assume the shape of the wound or body cavity.

* * * * *